United States Patent
Droeschel et al.

(10) Patent No.: US 12,208,460 B2
(45) Date of Patent: Jan. 28, 2025

(54) CUTTING TOOL

(71) Applicant: Ceratizit Luxembourg S.a.r.l., Mamer (LU)

(72) Inventors: Michael Droeschel, Mamer (LU); Michael Magin, Mamer (LU); Michael Sogaard, Mamer (LU); Luc Scheller, Mamer (LU)

(73) Assignee: CERATIZIT Luxembourg S.a.r.l., Mamer (LU)

( * ) Notice: Subject to any disclaimer, the term of this patent is extended or adjusted under 35 U.S.C. 154(b) by 427 days.

(21) Appl. No.: 17/620,843

(22) PCT Filed: May 28, 2020

(86) PCT No.: PCT/EP2020/064832
§ 371 (c)(1),
(2) Date: Dec. 20, 2021

(87) PCT Pub. No.: WO2020/254085
PCT Pub. Date: Dec. 24, 2020

(65) Prior Publication Data
US 2022/0402051 A1    Dec. 22, 2022

(30) Foreign Application Priority Data
Jun. 20, 2019 (EP) .................................. 19181566

(51) Int. Cl.
*B23D 61/00* (2006.01)
*B23D 61/02* (2006.01)

(52) U.S. Cl.
CPC ......... *B23D 61/006* (2013.01); *B23D 61/026* (2013.01)

(58) Field of Classification Search
CPC .............................. B23D 61/006; B23D 61/12
See application file for complete search history.

(56) References Cited

U.S. PATENT DOCUMENTS

| | | | |
|---|---|---|---|
| 4,617,930 A * | 10/1986 | Saunders | A61B 17/142 30/348 |
| 5,178,626 A | 1/1993 | Pappas | |
| 6,656,186 B2 | 12/2003 | Meckel | |
| 7,691,106 B2 * | 4/2010 | Schenberger | A61B 17/142 606/82 |
| 2010/0010492 A1 | 1/2010 | Lockard et al. | |

(Continued)

FOREIGN PATENT DOCUMENTS

| | | | | |
|---|---|---|---|---|
| DE | 102011078488 A1 * | 1/2013 | | B23D 61/006 |
| DE | 102013203613 A1 | 9/2014 | | |

(Continued)

*Primary Examiner* — Jennifer S Matthews
(74) *Attorney, Agent, or Firm* — Laurence A. Greenberg; Werner H. Stemer; Ralph E. Locher

(57) ABSTRACT

A cutting tool for severing a non-metallic material includes a holding element and a cutting element held on the holding element for cutting contact with the non-metallic material. A boundary region adjoins a holding material region of the holding element and a cutting material region of the cutting element. The precise severing of, for example, bone materials of human or animal origin, is possible in that a deformation resistance against an elastic deformation of the holding material region is greater than a deformation resistance against an elastic deformation of the cutting material region.

14 Claims, 11 Drawing Sheets

(56) References Cited

U.S. PATENT DOCUMENTS

2015/0096422 A1\* 4/2015 Stoddart .............. B23D 61/021
                                                     83/835
2019/0054552 A1   2/2019 Churchill
2020/0001494 A1\* 1/2020 Gisler .................. B23D 61/006

FOREIGN PATENT DOCUMENTS

| DE | 102013212594 A1 \* | 12/2014 | ........... B23D 61/006 |
| EP | 1558419 A2 | 8/2005 | |
| EP | 1558419 B1 \* | 6/2007 | ........... A61B 17/142 |
| EP | 2295211 B1 | 5/2017 | |
| WO | WO-2016132320 A1 \* | 8/2016 | |

\* cited by examiner

CUTTING TOOL

FIELD AND BACKGROUND OF THE INVENTION

The present invention relates to a cutting tool for severing a nonmetallic material, comprising a holding element, a cutting element, which is held on the holding element so as to make cutting contact with the nonmetallic material, and a boundary region, which adjoins a holding material region of the holding element and a cutting material region of the cutting element.

The present invention is in the field of the severing, in particular by setting a cutting tool of the type mentioned at the outset into an oscillating vibration of a frequency of, for example, 20,000 strokes per minute or more at a relatively small amplitude, of a nonmetallic material, in particular one which can usually be severed with a relatively low cutting force, in particular by machining, such as, for example, a wood or woods, a plastic or plastics, a fiber composite material or fiber composite materials, an organic material or organic materials, a gypsum or gypsums, a gas concrete or gas concretes, that is to say a porous concrete or concretes, in each case based on lime, lime cement or cement mortar, or a bone material or bone materials of in each case human or animal origin.

Accordingly, the cutting tools of the type mentioned at the outset include, in particular, corresponding saw blades or blades.

A cutting tool of the type mentioned at the outset in the form of a saw blade is already known from EP 2 295 211 B1. However, the severing of a nonmetallic material, in particular—but not only—if it is a bone material of human or animal origin, with such a cutting tool is made more difficult by the fact that it sometimes deviates in an uncontrolled manner from a parting or cutting direction which is usually—but not only—determined by means of manual guidance. Such a deviation may also be referred to as a break-out of the cutting tool.

SUMMARY OF THE INVENTION

It is therefore the object of the present invention to provide a cutting tool of the type mentioned at the outset by means of which it is possible to sever, in particular—but not only—bone materials of human or animal origin more precisely.

The cutting tool for severing a nonmetallic material comprises a holding element, a cutting element, which is held on the holding element so as to make cutting contact with the nonmetallic material, and a boundary region, which adjoins a holding material region of the holding element and a cutting material region of the cutting element, wherein a deformation resistance to an elastic deformation of the holding material region is greater than a deformation resistance to an elastic deformation of the cutting material region. As a result, the cutting tool is stabilized with respect to an elastic deformation in the region of the holding element, which can be formed, for example, in the shape of a plate, thus ensuring that the cutting element, which can have cutting teeth, is pressed against the more rigid holding element in the sense of an abutment during cutting, something that promotes, for example, cutting along a predetermined, in particular straight, parting line; this parting line can be marked, in particular on and/or in a bone, a wood workpiece, a plastic workpiece, a fiber composite workpiece, an organic workpiece, a gypsum workpiece or a gas concrete workpiece. This can be further improved if the cutting element is made shorter than the holding element along a longitudinal direction of the cutting tool, particularly if the cutting element and the holding element are each of plate-shaped configuration. The holding element and the cutting element are preferably connected to one another by material bonding. In this case, the boundary region comprises or consists of a bonding material, such as a solder and/or an adhesive material, or a material mixture comprising or consisting of materials of the holding element and of the cutting element and also optional further materials which are obtainable from a material bonding source, for example a welding medium, in particular a welding wire. The latter can be obtained, for example, by producing a welded joint between the holding element and the cutting element, according to which, in this example, the boundary region can be referred to as a weld seam or the like.

The holding material region and the cutting material region are preferably arranged opposite one another, in particular in a plan view of the cutting tool. The cutting element is thereby held even more stably.

The boundary region, which can also be referred to as the first boundary region, is, in particular, a region which is or can be formed, at least in some section or sections, on the basis of a nonpositive and/or positive and/or materially bonded joint between the holding element and the cutting element. In a plan view of the cutting tool, particularly if the holding element is of plate-shaped design, it is possible, in particular, to assign to a course of the boundary region a connecting line which extends within the boundary region, wherein the connecting line preferably connects at least two, preferably diametrical, outer edges of the cutting tool to one another. The connecting line preferably ends in at least one outer edge region of the cutting tool. The connecting line can be straight, curved, or straight in some section or sections, or curved in some section or sections. The connecting line can extend transversely or parallel to the longitudinal axis. The connecting line may also be assigned an orientation lying between these two orientations.

The boundary region can comprise a material mixing region or preferably consist of this. The material mixing region can preferably be based on, or preferably consist of, material of the holding material region and material of the cutting element region. As an alternative or in addition, the material mixing region can be based on, or preferably consist of, material of a bonding material, e.g. a solder and/or an adhesive material.

As a particular preference, the cutting tool is configured as an oscillating saw blade, wherein the oscillating saw blade can be set into oscillating vibration with a predetermined stroke by means of a drive shaft, in particular a motor shaft, of a drive unit, in particular of a motor, preferably of an electric motor, thus enabling the cutting element to be oscillated parallel and/or perpendicularly to a parting direction, which can also be referred to as the cutting direction, in the region of a free end, which can have a cutting edge and/or cutting teeth, which can also be referred to as saw teeth. This is because particularly precise oscillating partition of the nonmetallic material is made possible in this way.

Accordingly, it is even more preferred if the cutting tool formed as an oscillating saw blade is operatively connected to the motor, thus providing an oscillating saw in this way. As a particular preference, it is operatively connected to the motor via a transmission, in particular a transmission shaft of the transmission.

Making cutting contact means, in particular, that the nonmetallic material is machined.

Since the cutting tool comprises the holding element and the cutting element, it is accordingly of two-part design. However, a multi-part design with three or more elements, such as, for example, an additional connecting element for positive connection to a drive element of a drive unit, is also conceivable and also possible.

According to a further development of the cutting tool, the deformation resistance of the holding material region and the deformation resistance of the cutting material region are each a bending deformation resistance. According to this, the partition of the nonmetallic material is stabilized particularly against bending deformation. Such stabilization can be provided, in particular, in that the product of a modulus of elasticity of a material of the holding material region and an area moment of inertia of the holding material region is greater than the product of a modulus of elasticity of a material of the cutting material region and an area moment of inertia of the cutting material region. These products may also be referred to as the bending stiffnesses of the holding material region and of the cutting material region, respectively. In this case, the area moments of inertia are in each case preferably determined with respect to a bending axis which is defined in geometrical terms and is in each case positioned for its position along a longitudinal axis of the cutting tool with respect to the holding element and the cutting element, for example at half a height measured in the cross-sectional section of the holding element and of the cutting element in the case of a horizontal bending axis.

According to a further development of the cutting tool, the holding material region consists of a holding material and the cutting material region consists of a cutting material which is different from the holding material. This makes it possible, on the one hand, to increase the bending stiffness of the cutting tool by selecting the holding material on the basis of its modulus of elasticity for example, and, on the other hand, to select the cutting material on the basis of its suitability for optimizing the cutting element provided for making cutting contact with the nonmetallic material. The latter suitability can be expressed, for example, in that cutting teeth can be produced with defined cutting tooth flanks, in particular in a reproducible manner. Steel is particularly worthy of consideration as a cutting material for this purpose.

The holding element preferably consists of the holding material, contributing to even better stabilization of the cutting element during cutting.

The cutting element preferably consists of the cutting material, according to which, given a suitable choice of the cutting material, the cutting element can be selected for severing a specific nonmetallic material and/or for absorbing reaction forces and thermal loads which may act on the cutting element during cutting.

According to a further development of the cutting tool, a modulus of elasticity of the holding material is greater than a modulus of elasticity of the cutting material. This is an advantageous way of increasing the bending stiffness of the cutting tool while advantageously avoiding special structural measures. Thus, the modulus of elasticity of the holding material can be greater by a factor of 1.1 to 5 or more, for example, than the modulus of elasticity of the cutting material. Preferred values of this range, i.e. of the factor, are 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0.

The modulus of elasticity of the cutting material and of the holding material also relates, in particular, to the component or components of an elasticity tensor which can be assigned in each case to the cutting material and the holding material, said component or components being relevant for the respective elastic deformation of the cutting material region and of the holding material region, insofar as the cutting material and the holding material are elastically anisotropic.

The holding element preferably consists of the holding material region, contributing to even better stabilization of the cutting tool during cutting.

The cutting element preferably consists of the cutting material region, according to which, given a suitable choice of the cutting material region, the cutting element can be selected for severing a specific nonmetallic material and/or for absorbing corresponding reaction forces which may act on the cutting element during cutting.

According to a further development of the cutting tool, the holding material has a material matrix with a matrix ductility and hard material particles arranged in the material matrix with a particle ductility which is less than the matrix ductility. The holding material is thereby made available in the form of a composite material in order to further increase the bending stiffness and enhance the wear resistance of the cutting tool. The hard material particles can consist, for example, of tungsten carbide (WC) and the material matrix of cobalt (Co) or a mixed crystal based on cobalt (Co). Accordingly, the holding material is a hard metal (cemented carbide). The hard material particles of WC are preferably less than or equal to 20 µm, preferably less than or equal to 20 µm, 19 µm, 18 µm, 17 µm, 16 µm, 15 µm, 14 µm, 13 µm, 12 µm, 11 µm, 10 µm, 9 µm, 8 µm, 7 µm, 6 µm, 5 µm, 4 µm, 3 µm, 2 µm, 1 µm, 0.5 µm, 0.4 µm, 0.3 µm, 0.2 µm or 0.1 µm. The cobalt content, in elemental form or as mixed crystal, is preferably from 3 to 30 percent by weight, based on the total composition of the holding material (preferred values, i.e. percentages by weight, of this range are 3, 4, 5, 6, 7, 8, 9, 10, 11, 12, 13, 14, 15, 16, 17, 18, 19, 20, 21, 22, 23, 24, 25, 26, 27, 28, 29 or 30); the corresponding remainder is formed by the hard material particles of WC and optionally by other hard material particles such as vanadium carbide (VC), chromium carbide ($Cr_2C_3$) and/or tantalum-niobium carbide (Ta,Nb)C. Alternatively or in addition, the hard material particles can consist of titanium carbide (TiC), titanium nitride (TiN) and/or tantalum carbide (TaC) and the material matrix can consist of niobium (Nb), molybdenum (Mo) or cobalt (Co) or corresponding mixed crystals of these elements. Accordingly, the holding material is a cermet. The hard material particles of titanium carbide (TiC), titanium nitride (TiN) and/or tantalum carbide (TaC) are preferably less than or equal to 20 µm, preferably less than or equal to 20 µm, 19 µm, 18 µm, 17 µm, 16 µm, 15 µm, 14 µm, 13 µm, 12 µm, 11 µm, 10 µm, 9 µm, 8 µm, 7 µm, 6 µm, 5 µm, 4 µm, 3 µm, 2 µm, 1 µm, 0.5 µm, 0.4 µm, 0.3 µm, 0.2 µm or 0.1 µm. The niobium (Nb), molybdenum (Mo) or cobalt content (Co), in each case in elemental form or as mixed crystal, is preferably from 3 to 30 percent by weight, based on the total composition of the holding material (preferred values, i.e. percentages by weight, of this range are 3, 4, 5, 6, 7, 8, 9, 10, 11, 12, 13, 14, 15, 16, 17, 18, 19, 20, 21, 22, 23, 24, 25, 26, 27, 28, 29 or 30); the corresponding remainder is formed by the hard material particles of titanium carbide (TiC), titanium nitride (TiN) and/or tantalum carbide (TaC) and optionally other hard material particles. In the case of provision as a cermet, the holding material is preferably nickel-free.

According to a further development of the cutting tool, the holding material is a ceramic material, a refractory metal or a mixture thereof. The holding material is thereby made available to further increase bending stiffness. The refractory metal may be, for example, a molybdenum or tungsten metal, each of which may advantageously be subjected to forming or primary forming to give the holding element and, at the same time, has a relatively high modulus of elasticity for advantageously increasing bending stiffness. The ceramic may be, for example, an oxide ceramic based on aluminum oxide, magnesium oxide, zirconium oxide or titanium dioxide. The oxide ceramic is preferably an aluminum oxide ceramic reinforced with zirconium. Alternatively, the ceramic may be a substantially, preferably completely, oxide-free ceramic, i.e. in particular a ceramic based on carbides, nitrides, borides and/or silicides.

According to a further development of the cutting tool, the holding element is monolithic. According to this, a particularly flexurally stiff cutting tool is provided. Monolithic is intended, in particular, to mean that a homogeneous material path is formed from any desired end of the holding element to any other desired end of the holding element.

According to a further development of the cutting tool, the cutting material is a metallic material, in particular a steel, and a ductility of the cutting material is greater than a ductility of the holding material. The cutting material is thereby made available as a relatively ductile material in relation to the holding material, according to which, for example, the production of cutting teeth in and/or on a cutting element blank from which the cutting element can be produced or is produced is made possible with defined tooth flanks in a simplified, preferably reproducible, manner, in particular by stamping in combination with optional further production steps such as grinding, milling, sawing or the like. In this context, the ductility of the cutting material and of the holding material can be dimensioned on the basis of a uniform elongation or elongation at break obtainable from a tensile test. The elongation at break of the cutting material in the form of the metallic material, in particular of the steel, is preferably greater by at least a factor of 2 to 50 than the elongation at break of the holding material. Preferred values of this range, i.e. of the factor, are 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3 or 2.

According to a further development of the cutting tool, the holding material region and the cutting material region are connected to one another in a materially bonded manner by means of an adhesive joint, a soldered joint or a welded joint, in particular a beam welded joint. A particularly advantageous materially bonded connection between the holding material region and the cutting material region is thereby provided in each case. The beam welded joint means, in particular, that a melting energy required to melt the holding material and/or the cutting material can be obtained from one or more laser beams and/or electron beams.

According to a further development of the cutting tool, the boundary region is formed so as to extend between two outer edge points of the cutting tool. This is a particularly advantageous measure for the, in particular materially bonded, stable connection of the cutting element to the holding element. This being, for example, in the form of a weld seam or the like. The holding material region and the cutting element material region preferably extend between the two outer edge points.

According to a further development of the cutting tool, the boundary region ends in a first outer edge region of the cutting tool and in a second outer edge region of the cutting tool. This is a particularly advantageous measure for the, in particular materially bonded, stable connection of the cutting element to the holding element. The two outer edge regions can be arranged at the same or different longitudinal axis positions with respect to a longitudinal axis of the cutting tool. The two outer edge regions can be connected by means of a connecting line which is oriented parallel, perpendicular or at an angle other than 90°, for example 0° to 89°, preferably 1°, 2°, 3°, 4°, 5°, 10°, 15°, 20°, 25°, 30°, 35°, 40°, 45°, 50°, 55°, 60°, 65°, 70°, 75°, 85°, 89°, to a longitudinal axis of the cutting tool. The two outer edge regions can each preferably be surface regions of different side faces which are each preferably smaller than a surface, visible in a plan view of the holding element, of the holding element of the cutting tool, and which can be seen in corresponding side views of the cutting tool.

According to a further development of the cutting tool, at least two outer edge points of the cutting tool are arranged between the holding material region and the cutting material region in a plan view of the cutting tool. As a result, the holding material region advantageously forms, for example, a material bonding surface at which the cutting element can be or is connected to the holding element by material bonding. The outer edge points can be connected by means of a straight connecting line which runs perpendicularly to a longitudinal axis or runs obliquely to the longitudinal axis, in particular in a plane of the holding element, for example transversely thereto.

The material bonding surface, which is preferably an end face of the holding element, which can be of plate-shaped configuration, can make contact, substantially, preferably completely, without a gap, with a contact-making surface of the cutting element shaped in a manner corresponding to the latter, and accordingly it is possible to achieve a materially bonded joint between the cutting element and the holding element which is particularly advantageous because it maximizes contact. Accordingly, the material bonding surface and the contact-making surface can each preferably be in the form of flat surfaces or of a convex-concave pair of surfaces. In the latter case, the material bonding surface is preferably concave and the contact-making surface correspondingly convex.

According to a further development of the cutting tool, an outer region of the holding material region has a chamfer or an edge rounding, at least in some section or sections. These measures advantageously minimize the risk of an otherwise right-angled outer edge of the holding material region breaking, at least partially, and thus promoting further crack growth.

According to a further development of the cutting tool, two outer edges of the holding material region are connected by a convex chord. These measures advantageously minimize the risk of an otherwise right-angled outer edge of the holding material region breaking, at least partially, and thus promoting further crack growth.

According to a further development of the cutting tool, the cutting tool comprises a connecting element for positive connection to a drive element of a drive unit, wherein the connecting element is held on the holding element, a boundary region, which may also be referred to as the second boundary region to distinguish it from the boundary region adjoining the holding material region and the cutting material region, is formed between the connecting element and the holding element and a ductility of a connecting material of the connecting element is greater than a ductility of the holding material. When connected to the drive element, which can be, in particular, a motor shaft of an electric motor or an output shaft of a transmission connected to the motor shaft, the cutting tool is thereby made available in an advantageous manner. The connecting material is furthermore made available as a relatively ductile material in relation to the holding material, and accordingly the production of a recess for positive connection to the drive element, for example, is particularly simple, e.g. by stamping, sawing or milling. In this context, the ductility of the connecting material and of the holding material can be dimensioned on the basis of a uniform elongation or elongation at break obtainable from a tensile test. The elongation at break of the connecting material is preferably greater by at least a factor of 2 to 50 than the elongation at break of the holding material. Preferred values of this range, i.e. of the factor, are 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3 or 2. The connecting element is preferably plate-shaped. The connecting element and the holding element are preferably connected to one another in a positive-locking manner. A deformation resistance to an elastic deformation of a holding material region, adjoining the second boundary region, of the holding element is preferably greater than a deformation resistance to an elastic deformation of a connecting material region, adjoining the second boundary region, of the connecting element. The elastic deformation of the holding material region and the elastic deformation of the connecting material region are each preferably a bending deformation. Preferably, the holding material region consists of the holding material and the connecting material region consists of connecting material, which is different from the holding material. A modulus of elasticity of the holding material is preferably greater than a modulus of elasticity of the connecting material. The holding material is preferably a hard metal (cemented carbide), a cermet, a ceramic material, a refractory metal or a mixture thereof. The holding material region adjoining the second boundary region is preferably the holding material region adjoining the (first) boundary region. The connecting element is preferably monolithic.

According to a further development of the cutting tool, the connecting material is a metallic material, in particular a steel. This is advantageously a particularly easily machinable and relatively low-cost material for the production of a recess for positive connection to the drive element in the connecting element.

According to a further development of the cutting tool, the holding element and the connecting are connected to one another in a materially bonded manner by means of an adhesive joint, a soldered joint or a welded joint, in particular a beam welded joint. A particularly advantageous materially bonded connection between the holding element and the connecting element is thereby provided in each case. The beam welded joint means, in particular, that a melting energy required to melt the holding material and/or the connecting material can be obtained from one or more laser beams and/or electron beams.

According to a further development of the cutting tool, a first surface and a second surface adjoining the first surface are arranged so as to form an inner edge angle of less than 180° in a longitudinal section of the cutting tool. It is thereby advantageously possible to reduce the risk of collision of a drive unit connected to the cutting tool with the nonmetallic material, in particular for the purpose of achieving rectilinear guidance of the cutting tool if the cutting element makes, in particular virtually, surface contact with another component. This may also be referred to as an offset of the cutting tool. The inner edge angle, which can also be referred to as the first inner edge angle, is preferably less than or equal to 180°, 175°, 170°, 165°, 160°, 155°, 150°, 145°, 140°, 135°, 130°, 125°, 120°, 115°, 110°, 105°, 100°, 95° or 90°. The inner edge angle is preferably greater than 90° and less than 180°, including 175°, 170°, 165°, 160°, 155°, 150°, 145°, 140°, 135°, 130°, 125°, 120°, 115°, 110°, 105°, 100°, 95°. Accordingly, a jigsaw and/or plunge saw blade in the form of the cutting tool are/is preferably optionally provided. The first and the second surface are preferably surfaces of the optional connecting element and/or of the holding element. Preferably, one of the surfaces is a surface of the holding element and the other is a surface of the connecting element. Preferably, one of the surfaces is a surface of the holding element and the other is a surface of the cutting element.

According to a further development of the cutting tool, an axial dimension of the boundary region and/or of the second boundary region is less than an axial dimension of the holding element. It is thereby advantageously possible to provide localization of the elastic deformation, e.g. in the form of a maximum of a bending line, outside the boundary region or the second boundary region. The term "axial dimension" is used, in particular, to mean a dimension measured parallel to a longitudinal axis of the cutting tool.

According to a further development of the cutting tool, an axial dimension of the holding element is greater than or equal to an axial dimension of the cutting element. The bending stiffness of the cutting tool is thereby advantageously enhanced even further. The term "axial dimension" is used, in particular, to mean a dimension measured parallel to a longitudinal axis of the cutting tool.

According to a further development of the cutting tool, the boundary region and/or second boundary region is or are linear, in particular in a plan view of the cutting tool. Accordingly, the boundary region or the second boundary region is, for example, a weld seam or a solder seam or an adhesive seam.

According to a further development of the cutting tool, the holding element has a taper, preferably transversely to a longitudinal axis of the cutting tool. This is a particularly advantageous shape of the holding element. The taper is preferably formed at the boundary region and/or second boundary region.

According to a further development of the cutting tool, the cutting element has cutting teeth. The cutting performance of the cutting tool is thereby advantageously enhanced. The cutting teeth preferably form a row of cutting teeth comprising, for example, at least 10 or more, for example more than 20, 30, 40, 50, 60, 70, 80, 90, 100, 110, 120, 130, 140, 150, 160, 170, 180, 190, 200, 250, 300, 350, 400, 500, 600, 700, 800, 900 or 1000 cutting teeth, triangular teeth tapering to a point toward the outside. A boundary line, which can preferably be straight or round, can preferably be assigned to the row of cutting teeth. The cutting teeth are preferably arranged offset with respect to one another.

According to a further development of the cutting tool, the cutting tool is designed so that it can be guided manually. As a result, the cutting tool can be guided along a cutting line, in particular by means of a relatively low expenditure of force. According to this development, the cutting tool can preferably be connected to a hand-guided machine tool and/or to an electric power tool in a manner that allows guidance by hand.

According to a further development, the cutting tool is preferably of plate-shaped design. This is a shape which is particularly easy to produce.

According to a further development of the cutting tool, a thickness dimension can be assigned to it in a side view, a corresponding thickness preferably being variable along a longitudinal axis of the cutting tool, in particular in the region of the holding element and/or of the cutting element and/or of the connecting element. The thickness is preferably greater in the region of the connecting element than in the region of the cutting element. This contributes to further stabilization of the cutting tool. Alternatively, the thickness can be constant in each case in the region of the holding element and of the cutting element and optionally in the region of the connecting element, it preferably being possible for the thickness in the region of the holding element to be different from the thickness in the region of the cutting element and/or of the connecting element. If the thickness in these regions is the same in terms of magnitude, the cutting tool can be produced at particularly low cost, in particular by means of grinding or the like.

According to a further development of the cutting tool, a width dimension, i.e. width, can be assigned to it in a plan view, a corresponding width preferably being variable along a longitudinal axis of the cutting tool, in particular in the region of the holding element and/or of the cutting element and/or of the connecting element. The width is preferably greater in the region of the connecting element than in the region of the cutting element. This contributes to further stabilization of the cutting tool. Alternatively, the width can be constant in each case in the region of the holding element and of the cutting element and optionally in the region of the connecting element, it preferably being possible for the width in the region of the holding element to be different from the width in the region of the cutting element and/or of the connecting element.

According to a further development of the cutting tool, a width dimension, i.e. width, can be assigned to it in a plan view and a thickness dimension, i.e. thickness, can be assigned to it in a side view, a corresponding width and a corresponding thickness preferably being variable along a longitudinal axis of the cutting tool, in particular in the region of the holding element and/or of the cutting element and/or of the connecting element. The width and/or the thickness is preferably greater in the region of the connecting element than in the region of the cutting element. This contributes to further stabilization of the cutting tool. Alternatively, the width and/or thickness can be constant in each case in the region of the holding element and of the cutting element and optionally in the region of the connecting element, it preferably being possible for the thickness and/or width in the region of the holding element to be different from the thickness and/or width in the region of the cutting element and/or of the connecting element.

Further advantages and expedient features of the invention will become apparent from the following description of exemplary embodiments with reference to the attached figures.

DETAILED DESCRIPTION OF THE INVENTION

In FIGS. 1 to 11, identical, similar or identically acting elements are designated by identical reference signs and a repeated description of these elements is dispensed with in the following description in order to avoid redundancies.

Figure 1:
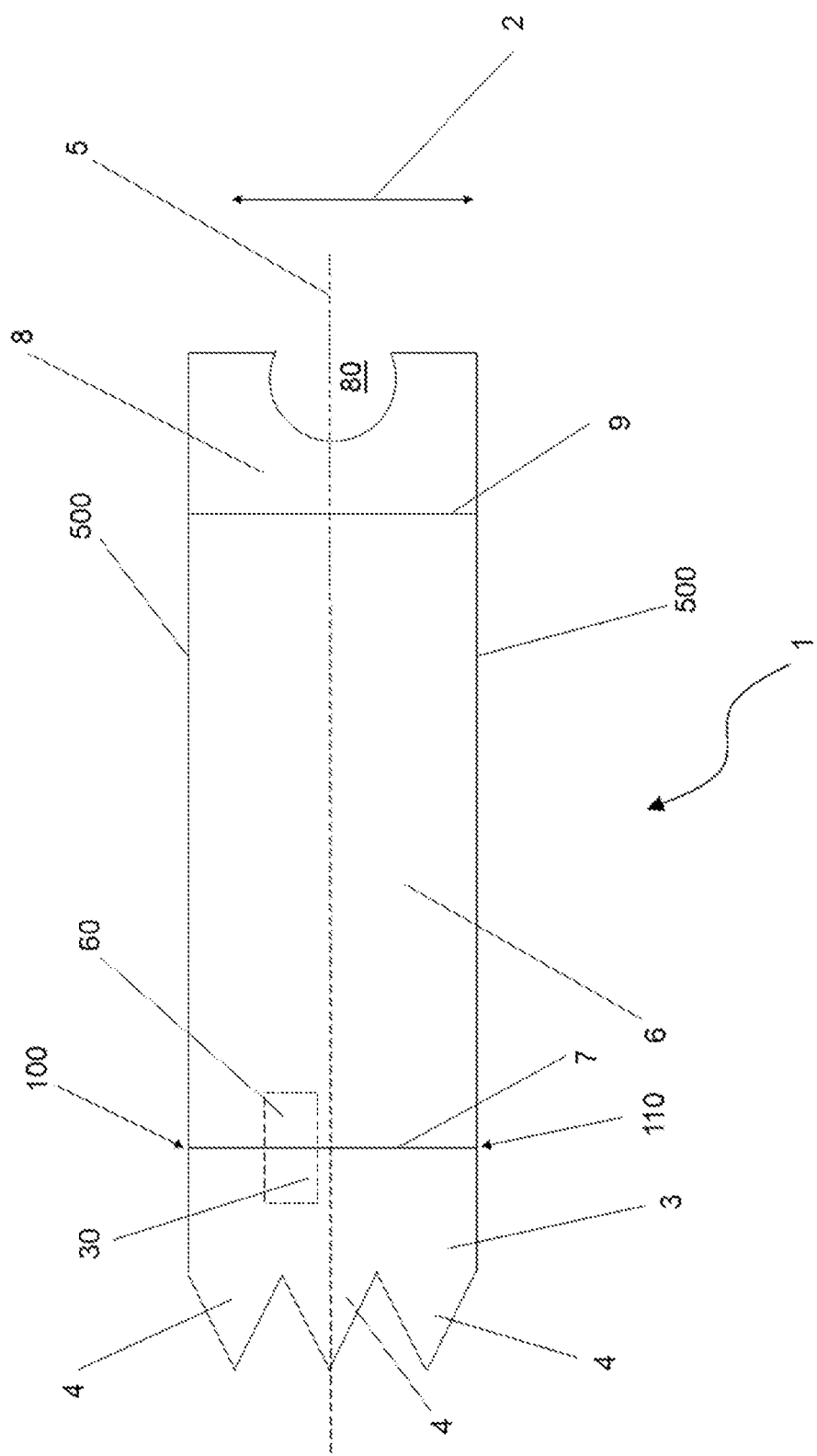
FIG. 1: shows a schematic illustration of a cutting tool according to a first embodiment in plan view.
Figure 2:
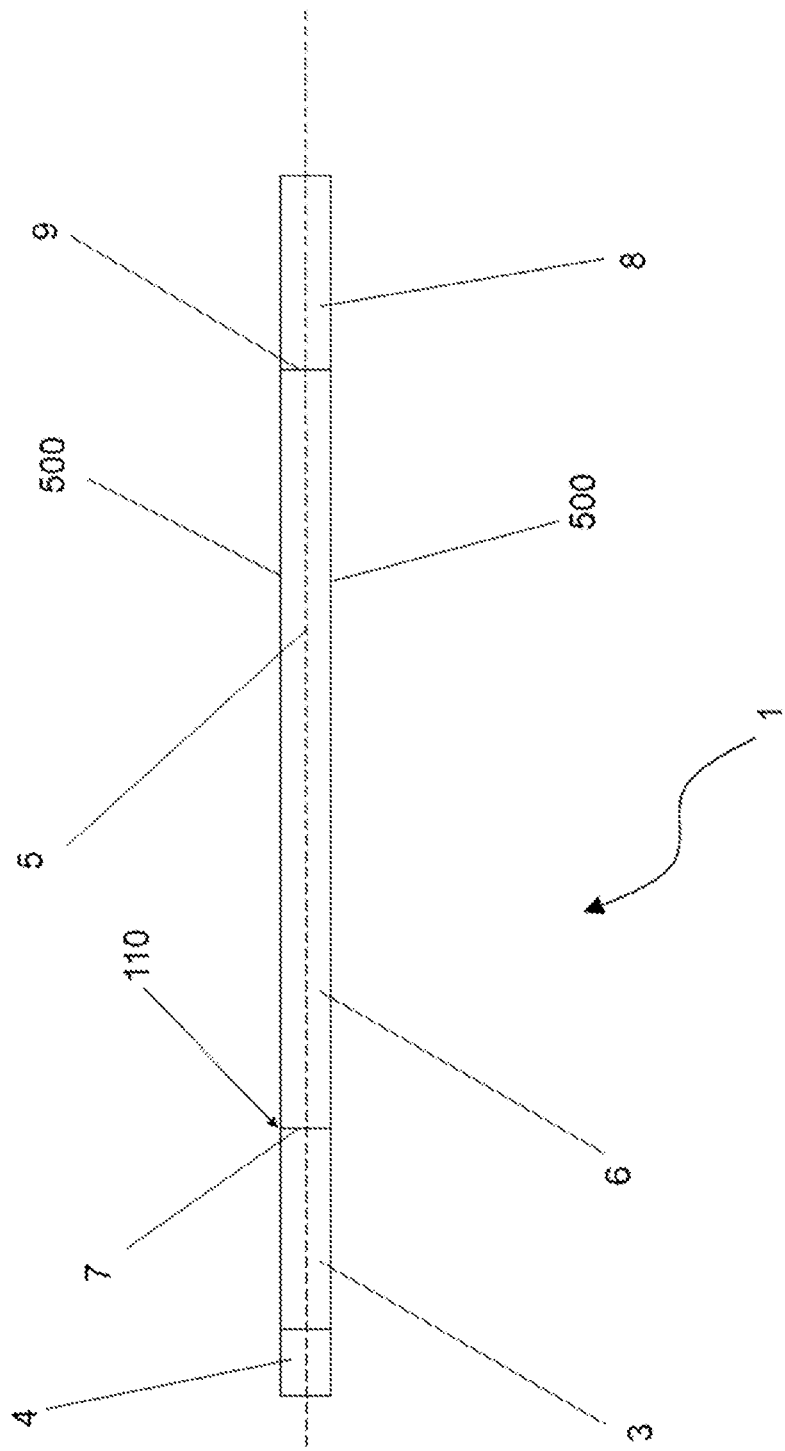
FIG. 2: shows a schematic illustration of the cutting tool according to FIG. 1 in a side view.

FIGS. 1 and 2 show a schematic illustration of a plate-shaped cutting tool 1 according to a first embodiment in plan view and in side view respectively. The cutting tool 1 is in the form of an oscillating saw blade which can be moved in an oscillating manner along the directions 2 at a frequency of, for example, 20,000 strokes per minute. During such an oscillation, a plate-shaped tool bit 3, which consists of a steel, is brought into contact with a nonmetallic material, for example a wood or a bone material. In the process, cutting of the nonmetallic material is performed by means of triangular cutting teeth 4 of the tool bit 3, the number of teeth that can be seen in FIG. 1 being chosen merely by way of example. Here, a corresponding cutting depth or feed can be set by an axial movement parallel to a longitudinal axis 5 of the cutting tool 1 in the direction of the cutting teeth 4. The tool bit 3 is materially connected to a holding plate 6 by a weld seam 7. The weld seam 7, whose extent in the axial direction is substantially less than that of the holding plate 6 and the tool bit 3, thus forms a boundary region, which may also be referred to as a connecting region, between the tool bit 3 and the holding plate 6. As a result, the holding plate 6 can absorb the forces which occur during machining and which may also be referred to as cutting reaction forces. The holding plate 6 is monolithic and consists of a hard metal (cemented carbide) with a modulus of elasticity of $650 \cdot 10^9$ N/m$^2$; however, other materials are also conceivable and also possible within the scope of the present disclosure. The tool bit 3 is likewise monolithic, being made of a steel having a modulus of elasticity of $210 \cdot 10^9$ N/m$^2$. Hence, the region 60 of the holding plate 6 which adjoins the weld seam 7 is more resistant to bending than the region 30 of the tool bit 3 which adjoins the weld seam 7. The effect is that the holding plate 7 counteracts a deflection of the cutting element 4 in one of the directions perpendicular to the longitudinal axis 5, for example in the directions 2 or one of the directions which are oriented perpendicularly to the plane of the drawing in FIG. 1, and parallel thereto, thus reducing the influence of cutting reaction forces, which can act on the tool bit 3 in the region of the cutting teeth 4, on the position of the tool bit 3 with respect to a fixed reference point located outside the cutting tool 1. The reference point can thus be assigned, for example, to a clamping device for clamping and holding the nonmetallic material. Since the tool bit 3 consists of a steel, the cutting teeth 4 can be produced by stamping with subsequent grinding.

FIG. 1 shows particularly clearly that the weld seam 7 extends over the entire width of the holding plate 7 and the tool bit 3, is linear and is oriented perpendicularly to the longitudinal axis (some other orientation is also conceivable and also possible, in the case of a different tool bit 3 and/or a different holding plate 6, for example, parallel to the longitudinal axis 5 or inclined with respect to the longitudinal axis 5, that is to say extending obliquely in the latter case). Geometrically speaking, the weld seam 7 can therefore be considered as a connecting line between two points 100 and 110 of corresponding outer edges 500 of the cutting tool 1.

The holding plate 6 is furthermore connected to a connecting plate 8 by another weld seam 9. The connecting plate 8 is likewise monolithic, being made of a steel having a modulus of elasticity of $210 \cdot 10^9$ N/m². Since the connecting plate 8 is made of steel, a concave recess 80 in the connecting plate 8 can be obtained by stamping, wherein the recess 80 is shaped to correspond to a drive shaft (not illustrated) of an electric motor, allowing the cutting tool 1 to be driven by means of the electric motor in order to carry out the oscillating movements in the directions 2. In this way, an electric power tool is made available.

FIG. 2 shows particularly clearly that the cutting tool 1 has a constant thickness, which may also be referred to as plate thickness, which consequently is the same in terms of magnitude in the region of the tool bit 3, the holding plate 6 and the connecting plate 8.

Figure 3:
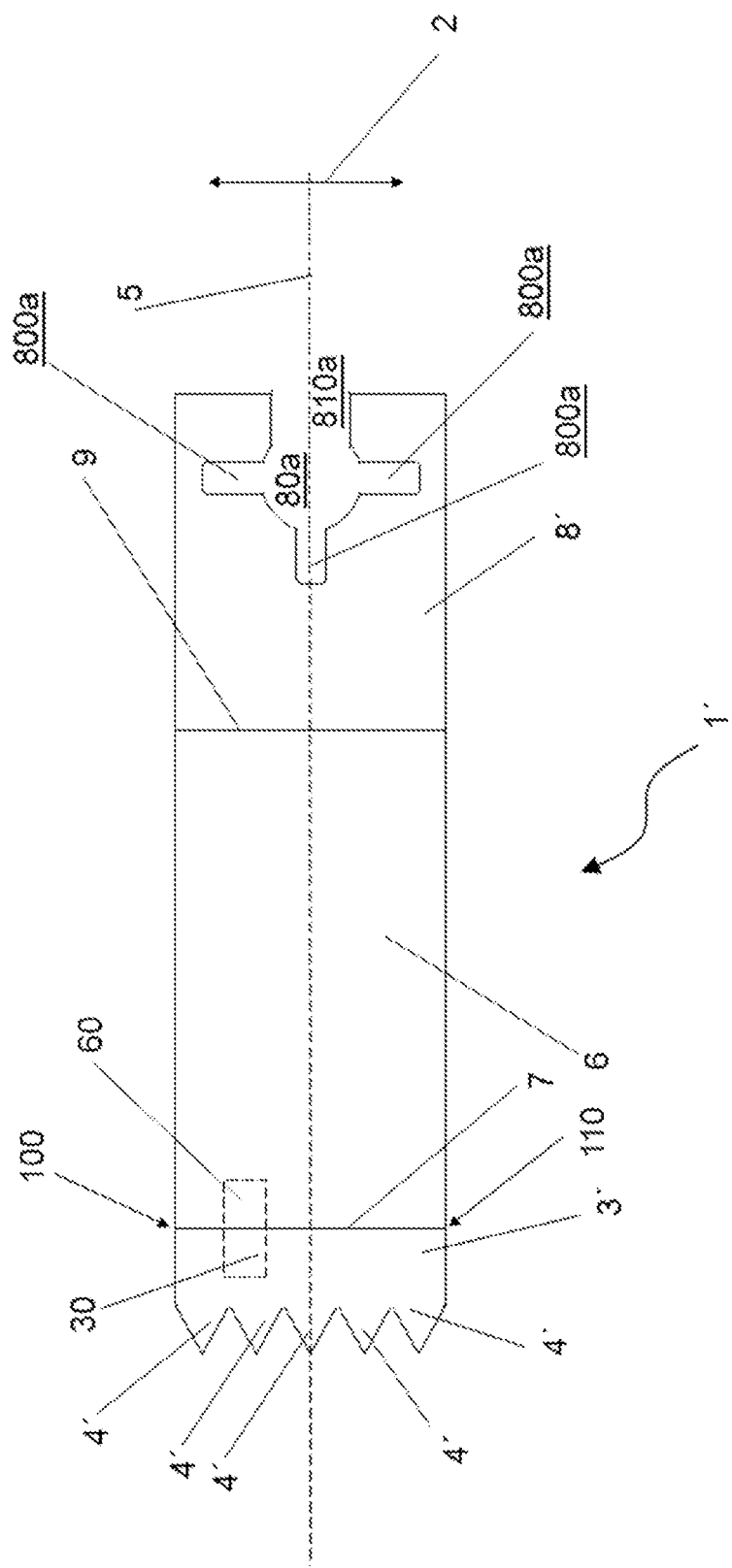
FIG. 3: shows a schematic illustration of a cutting tool according to a second embodiment in plan view.

FIG. 3 shows a schematic illustration of a plate-shaped cutting tool 1' according to a second embodiment in plan view and in side view respectively. Cutting tool 1' is of similar construction to cutting tool 1, wherein, in contrast to cutting tool 1, a connecting plate 8', which consists of the steel of the connecting plate 8, has a recess 80a with radial projections 800a and an axial plug-in slot 810a, which are shaped to correspond to a drive shaft (not illustrated) of the electric motor, in order to transmit more positive-locking forces to the cutting tool 1' than recess 80. Furthermore, connecting plate 8' is longer in the axial direction than the connecting plate 8 of cutting tool 1, increasing the surface contact with a clamping device of an electric power tool drive unit. Furthermore, tool bit 3' is shorter in the axial direction than tool bit 3, making tool bit 4' more flexurally rigid. By way of example, the number of cutting teeth 4' is greater than the number of cutting teeth 4.

Figure 4:
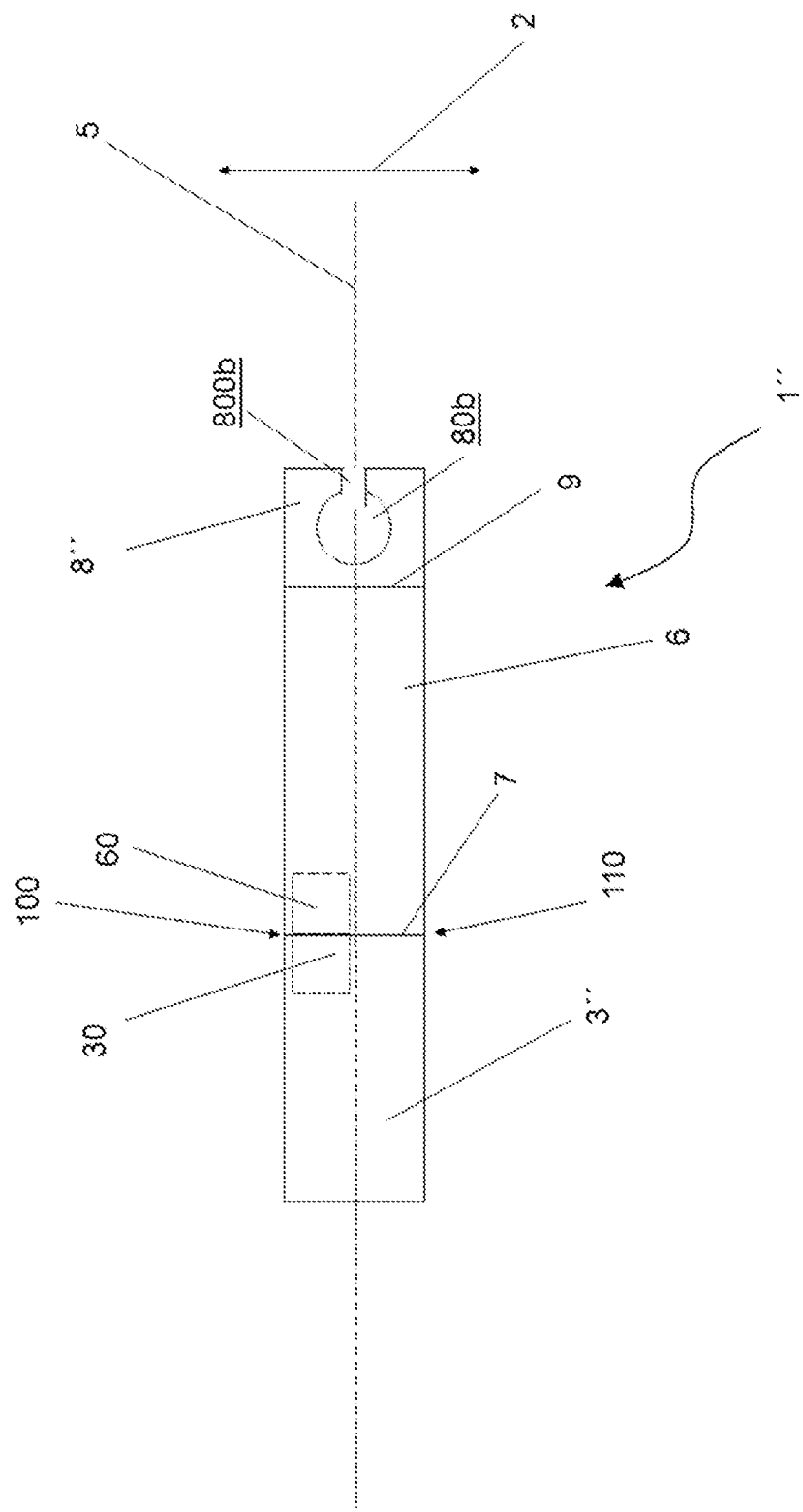
FIG. 4: shows a schematic illustration of a cutting tool according to a third embodiment in plan view.
Figure 5:
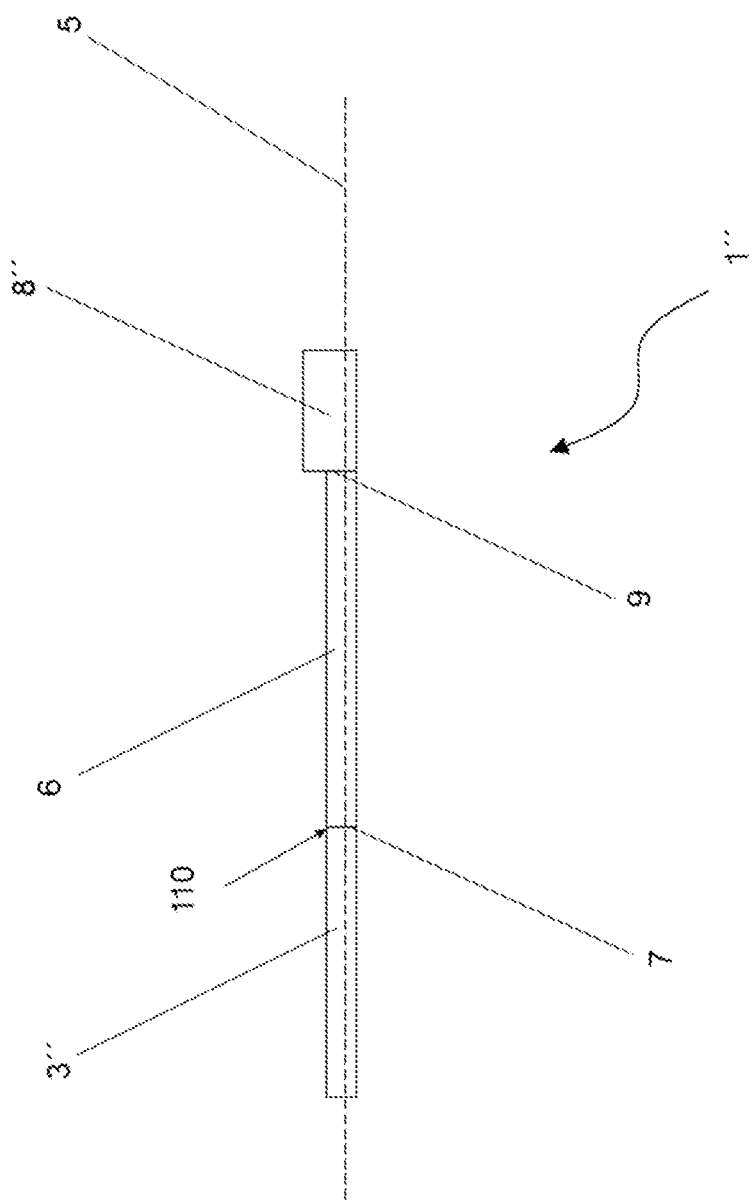
FIG. 5: shows a schematic illustration of the cutting tool according to FIG. 4 in a side view.

FIGS. 4 and 5 show a schematic illustration of a plate-shaped cutting tool 1" according to a third embodiment in plan view and in side view respectively. Cutting tool 1" is of similar construction to cutting tool 1, wherein cutting element 3", which consists of the steel of cutting element 3, is illustrated without cutting teeth, and a connecting plate 8", which consists of the steel of connecting plate 8, has a recess 80b with a plug-in slot 800b.

FIG. 5 shows particularly clearly that the cutting tool 1" has a constant thickness, which may also be referred to as plate thickness, in the region of the tool bit 3" and the holding plate 6 which is the same in magnitude in these regions, and has a constant thickness, i.e. plate thickness, in the region of connecting plate 8" which is greater than the plate thickness in the regions of the tool bit 3" and the holding plate 6.

Figure 6:
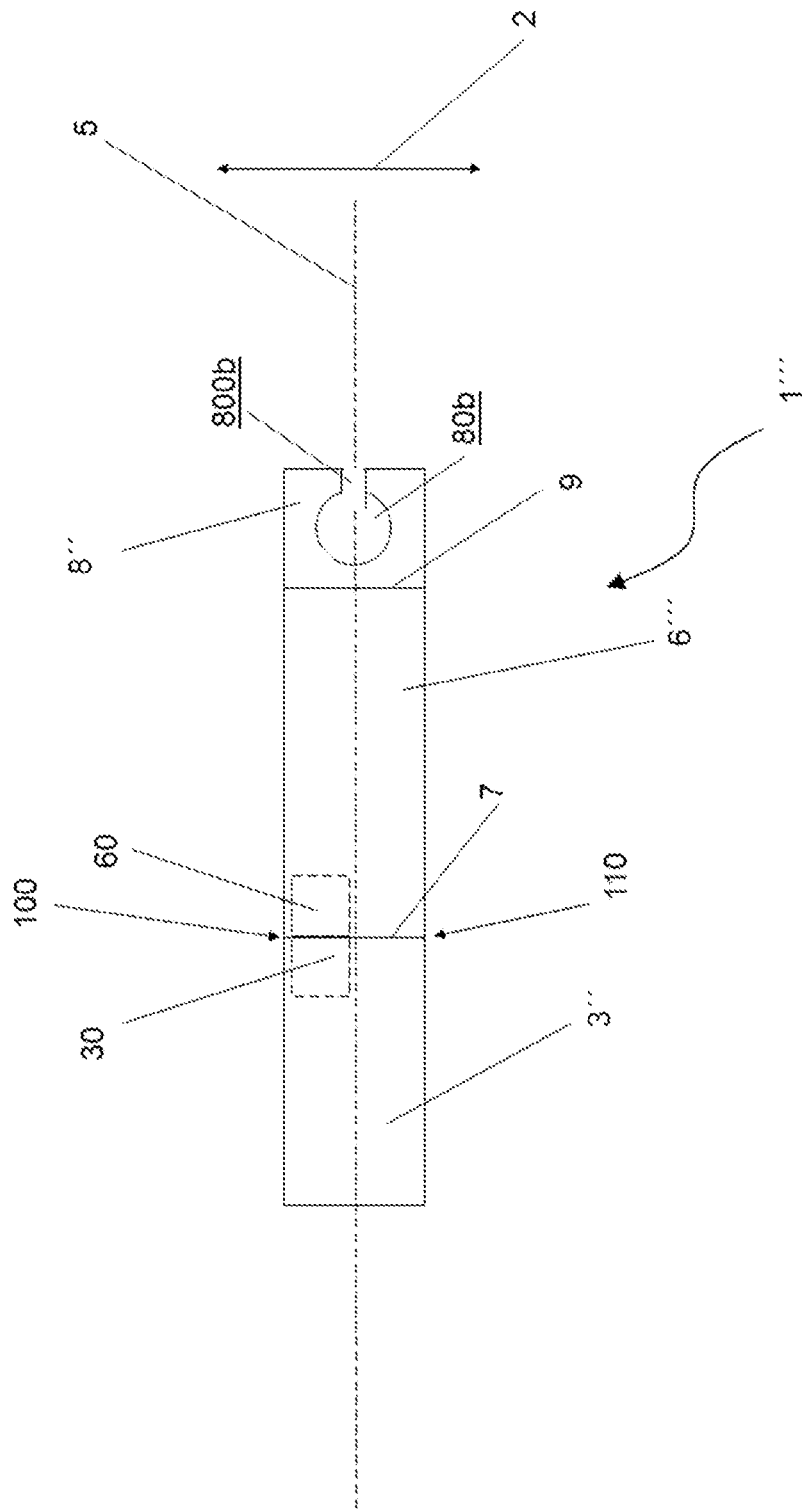
FIG. 6: shows a schematic illustration of a cutting tool according to a fourth embodiment in plan view.
Figure 7:
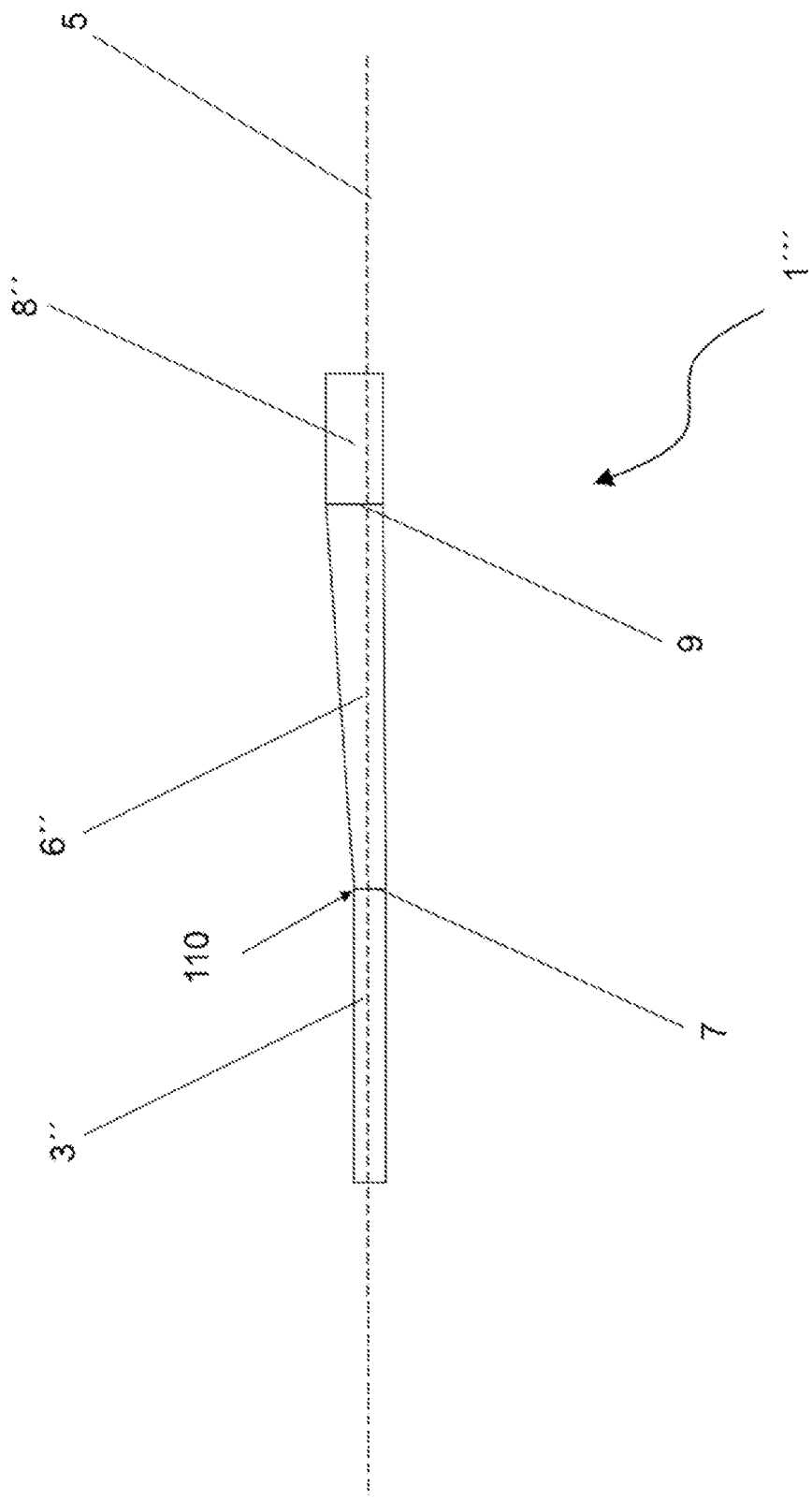
FIG. 7: shows a schematic illustration of the cutting tool according to FIG. 6 in a side view.

FIGS. 6 and 7 show a schematic illustration of a plate-shaped cutting tool 1''' according to a fourth embodiment in plan view and in side view respectively. Cutting tool 1''' is of similar construction to cutting tool 1", wherein, as can be seen particularly clearly from FIG. 7, a thickness, that is to say plate thickness, of cutting tool 1''' in the region of a holding plate 6''', beginning at the weld seam 7 with a thickness which corresponds to the thickness of tool bit 3", increases continuously until the thickness of the connecting plate 8" at the weld seam 9 is reached. In this case, holding plate 6''' consists of the hard metal (cemented carbide) of holding plate 6.

Figure 8:
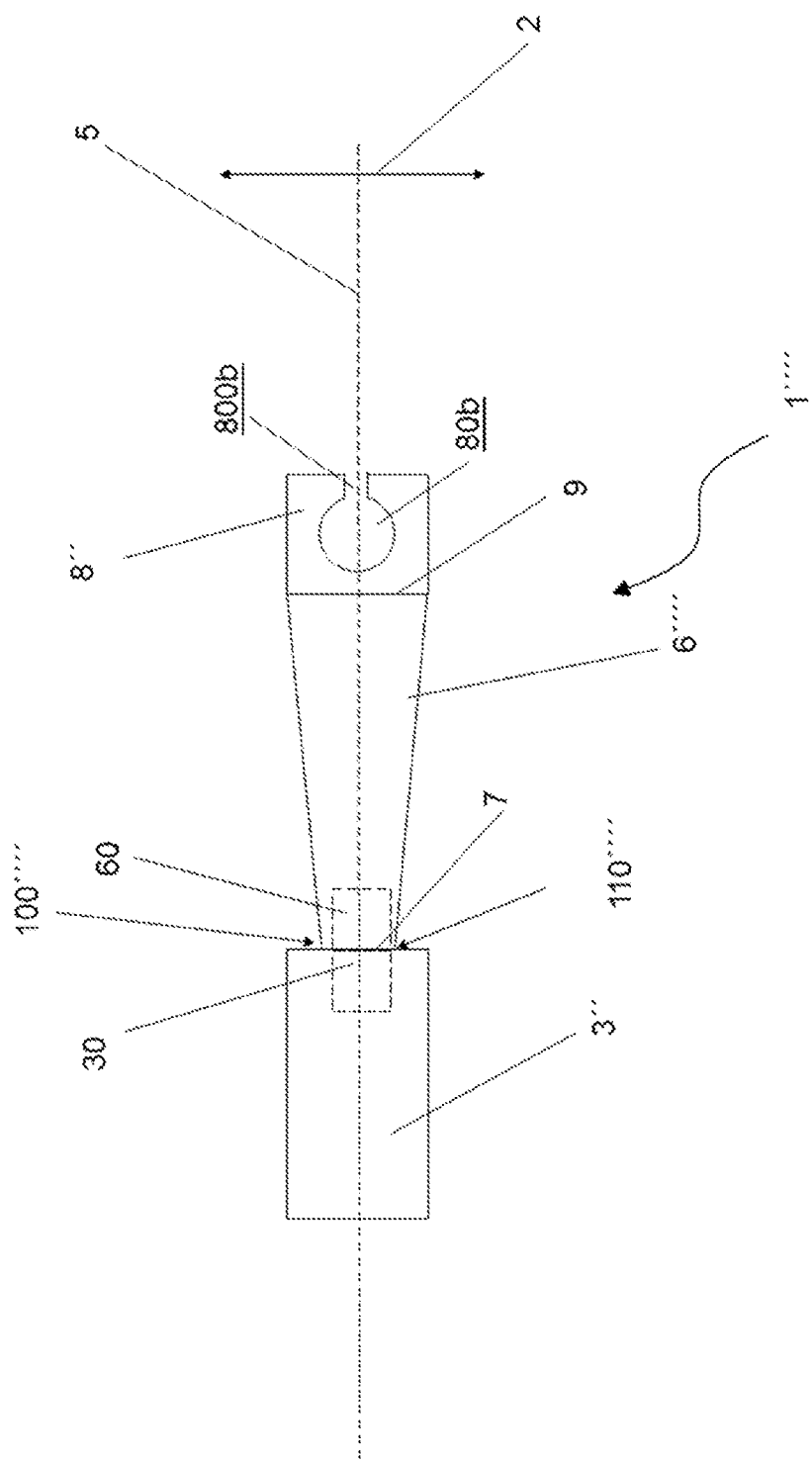
FIG. 8: shows a schematic illustration of a cutting tool according to a fifth embodiment in plan view.
Figure 9:
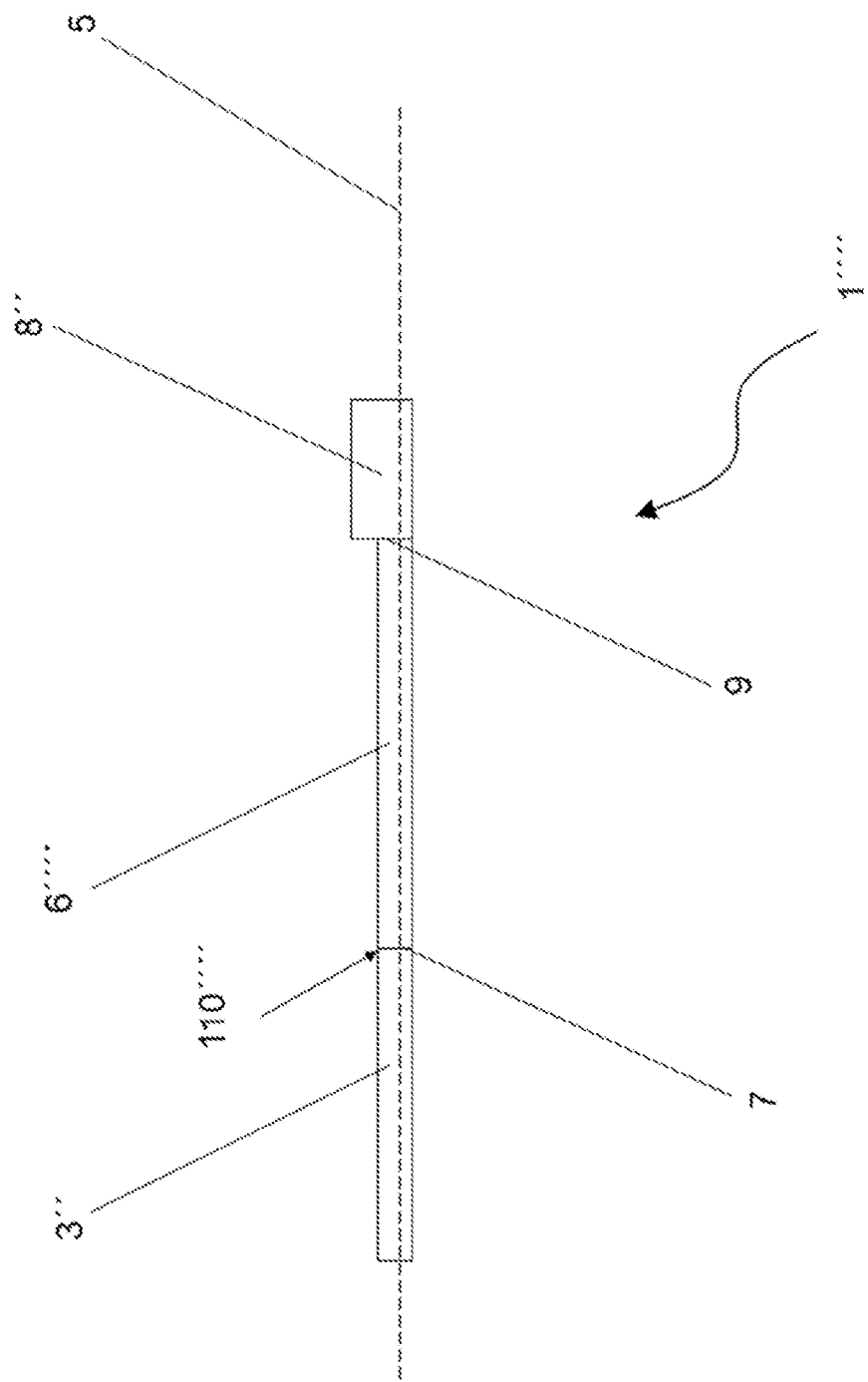
FIG. 9: shows a schematic illustration of the cutting tool according to FIG. 8 in a side view.

FIGS. 8 and 9 show a schematic illustration of a plate-shaped cutting tool 1'''' according to a fifth embodiment in plan view and in side view respectively. Cutting tool 1'''' is of similar construction to cutting tool 1''', wherein, as can be seen particularly clearly from FIG. 8, a holding plate 6'''' has a width which is dimensioned transversely to the longitudinal axis 2 and which becomes continuously smaller from weld seam 9 to weld seam 7; at weld seam 9, the width corresponds to a similarly dimensioned width of the connecting plate 8". Accordingly, the cutting tool 1'''' has a taper, specifically in the region of the holding plate 6''''. At weld seam 7, the width of the holding plate 6'''' corresponds to the distance between points 100'''' and 110'''' of corresponding outer edges of the cutting tool 1''''. In this case, holding plate 6'''' consists of the hard metal (cemented carbide) of holding plate 6.

Figure 10:
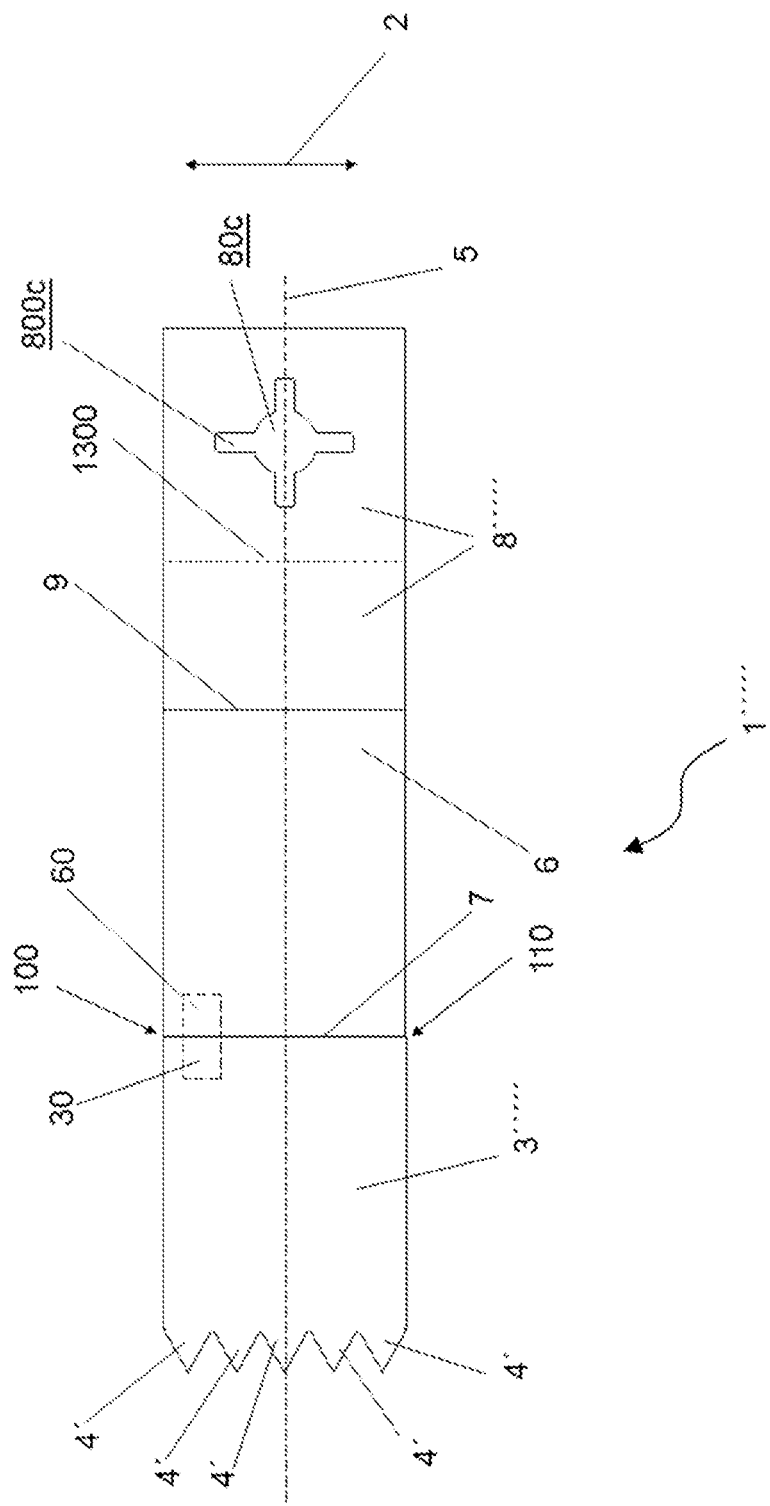
FIG. 10: shows a schematic illustration of a cutting tool according to a sixth embodiment in plan view.
Figure 11:
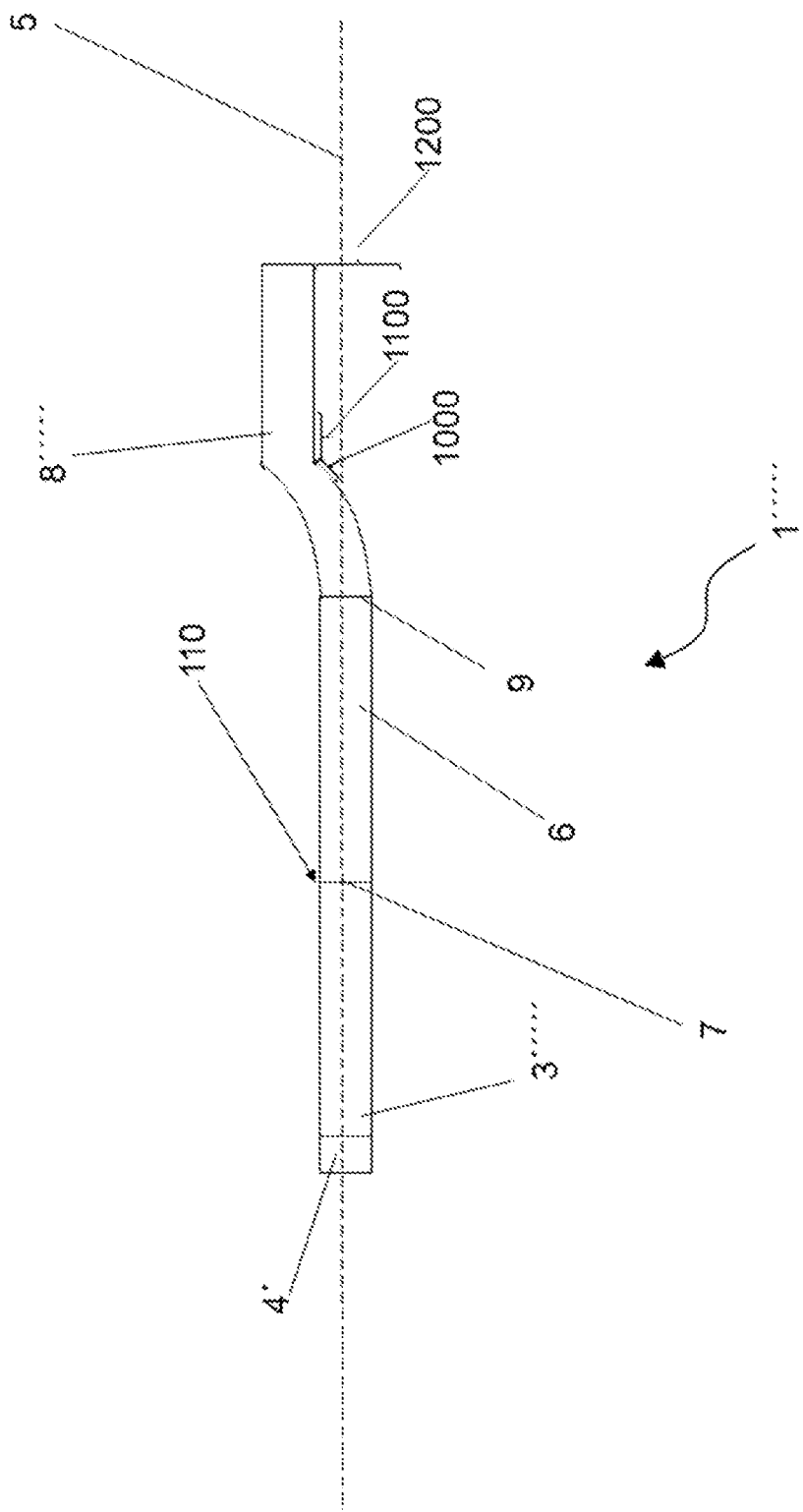
FIG. 11: shows a schematic illustration of the cutting tool according to FIG. 10 in a side view.

FIGS. 10 and 11 show a schematic illustration of a plate-shaped cutting tool 1''''' according to a sixth embodiment in plan view and in side view respectively. Cutting tool 1''''' is of similar construction to cutting tool 1', wherein, as can be seen particularly clearly from FIG. 11, a connecting plate 8''''', which consists of the steel of connecting plate 8, two mutually adjacent surfaces 1000 and 1100, which can be seen in profile in the side view according to FIG. 11 analogously to a corresponding longitudinal section, form an inner edge angle of 135°. Thus, cutting tool 1''''' is cranked in such a way in the region of the connecting plate 8''''' that a clearance 1200 (visible in FIG. 11) is obtained transversely to the longitudinal axis 5 in the region of the connecting plate 8''''', as compared with cutting tool 1 for example, enabling the clearance 1200 to be used to provide additional assembly space for connection to an electric motor of a drive unit or the like, it being possible, while remaining within the clearance 1200, for a tool bit 3''''' simultaneously to make contact with a base or the like parallel to its areal extent (visible in FIG. 10). A transition from surface 1000 to surface 1100 or vice versa is indicated in FIG. 10 by a dashed line 1300, which extends parallel to a transverse axis. Connecting plate 8''''' has a radially closed recess 80c with projections 800c for positive connection to a shaft of an electric motor.

Tool bit 3''''', which consists of the steel of tool bit 3, is longer than tool bit 3' in order to obtain axial machining space for severing the nonmetallic material.

The invention claimed is:
1. A cutting tool for severing a nonmetallic material, the cutting tool comprising:
   a holding element;
   a cutting element held on said holding element, said cutting element being configured for cutting contact with the non-metallic material; and
   a boundary region adjoining a holding material region of said holding element and a cutting material region of said cutting element, said holding material region having a deformation resistance to an elastic deformation greater than a deformation resistance to an elastic deformation of said cutting material region; and
   said holding material region consisting of a holding material and said cutting material region consisting of a cutting material, said cutting material being different from said holding material, and said cutting material being steel;

a modulus of elasticity of said holding material is greater than a modulus of elasticity of said cutting material, and said holding material having a material matrix with a matrix ductility and wherein hard material particles are disposed in said material matrix with a particle ductility which is less than the matrix ductility.

2. The cutting tool according to claim 1, wherein the deformation resistance of said holding material region and the deformation resistance of said cutting material region are a bending deformation resistance.

3. The cutting tool according to claim 1, wherein said holding material is a material selected from the group consisting of a ceramic material, a refractory metal, and a mixture thereof.

4. The cutting tool according to claim 1, wherein said holding element is monolithic.

5. The cutting tool according to claim 1, wherein said cutting material is a metallic material and a ductility of said cutting material is greater than a ductility of said holding material.

6. The cutting tool according to claim 1, wherein said holding material region and said cutting material region are connected to one another by way of material bonding with a joint selected from the group consisting of an adhesive joint, a soldered joint, and a welded joint.

7. The cutting tool according to claim 1, wherein said holding material region and said cutting material region are connected to one another by way of a beam welded joint.

8. The cutting tool according to claim 1, wherein said boundary region is formed to extend between two outer edge points of the cutting tool.

9. The cutting tool according to claim 1, wherein two outer edges of said holding material region are connected by a convex chord.

10. The cutting tool according to claim 1, which further comprises a connecting element for positive connection to a drive element of a drive unit, said connecting element being held on said holding element, with a boundary region being formed between said connecting element and said holding element, and a ductility of a connecting material of said connecting element being greater than a ductility of said holding material.

11. The cutting tool according to claim 10, wherein said connecting material of said connecting element is a metallic material.

12. The cutting tool according to claim 11, wherein said connecting material is a steel.

13. The cutting tool according to claim 10, wherein said holding element and said connecting element are connected to one another by way of material bonding with a joint selected from the group consisting of an adhesive joint, a soldered joint, and a welded joint.

14. The cutting tool according to claim 10, wherein said holding element and said connecting element are connected to one another by way of a beam welded joint.

* * * * *